United States Patent
Kostrzewski

(10) Patent No.: US 10,945,742 B2
(45) Date of Patent: Mar. 16, 2021

(54) ANTI-SKID SURGICAL INSTRUMENT FOR USE IN PREPARING HOLES IN BONE TISSUE

(71) Applicant: GLOBUS MEDICAL, INC., Audubon, PA (US)

(72) Inventor: Szymon Kostrzewski, Lausanne (CH)

(73) Assignee: GLOBUS MEDICAL INC., Audubon, PA (US)

(*) Notice: Subject to any disclaimer, the term of this patent is extended or adjusted under 35 U.S.C. 154(b) by 0 days.

(21) Appl. No.: 16/431,876

(22) Filed: Jun. 5, 2019

(65) Prior Publication Data

US 2019/0350596 A1    Nov. 21, 2019

Related U.S. Application Data

(63) Continuation of application No. 14/799,170, filed on Jul. 14, 2015, now Pat. No. 10,357,257.

(60) Provisional application No. 62/024,402, filed on Jul. 14, 2014.

(51) Int. Cl.
| | | |
|---|---|---|
| A61B 17/16 | (2006.01) | |
| A61B 34/20 | (2016.01) | |
| A61B 34/30 | (2016.01) | |
| A61B 90/00 | (2016.01) | |

(52) U.S. Cl.
CPC ........ *A61B 17/1615* (2013.01); *A61B 17/162* (2013.01); *A61B 17/1624* (2013.01); *A61B 34/20* (2016.02); *A61B 34/30* (2016.02); *A61B 2017/1602* (2013.01); *A61B 2090/035* (2016.02); *A61B 2090/3983* (2016.02)

(58) Field of Classification Search
CPC ............ A61B 17/1615; A61B 17/1617; A61B 17/162; A61B 17/1622; A61B 17/1624; A61B 17/17; A61B 17/1703; A61B 34/20
See application file for complete search history.

(56) References Cited

U.S. PATENT DOCUMENTS

| | | | |
|---|---|---|---|
| 4,150,293 | A | 4/1979 | Franke |
| 4,710,075 | A | 12/1987 | Davison |
| 5,246,010 | A | 9/1993 | Gazzara et al. |
| (Continued) | | | |

FOREIGN PATENT DOCUMENTS

| | | | |
|---|---|---|---|
| CN | 102085110 A | 6/2011 | |
| CN | 103767759 A | 5/2014 | |
| (Continued) | | | |

OTHER PUBLICATIONS

US 8,231,638 B2, 07/2012, Swarup et al. (withdrawn)

*Primary Examiner* — Anu Ramana

(57) ABSTRACT

Described herein is an anti-skid surgical instrument for use in preparing holes in bone tissue. The disclosed surgical instrument provides the ability to prepare a precise hole in bone tissue during surgery (e.g., spinal surgeries and pedicle screw placement, intramedullary screw placement). The disclosed surgical instrument accomplishes precise hole placement regardless of whether the angle between the drill axis and surface of the bone tissue is perpendicular. The disclosed technology includes a flat drilling surface which is perpendicular to the surface of the body of the surgical instrument. This reduces the likelihood of the surgical instrument skidding on the surface of the bone tissue and thereby increases the precision of the hole.

19 Claims, 2 Drawing Sheets

(56) References Cited

U.S. PATENT DOCUMENTS

| | | |
|---|---|---|
| 5,354,314 A | 10/1994 | Hardy et al. |
| 5,397,323 A | 3/1995 | Taylor et al. |
| 5,598,453 A | 1/1997 | Baba et al. |
| 5,772,594 A | 6/1998 | Barrick |
| 5,791,908 A | 8/1998 | Gillio |
| 5,820,559 A | 10/1998 | Ng et al. |
| 5,825,982 A | 10/1998 | Wright et al. |
| 5,887,121 A | 3/1999 | Funda et al. |
| 5,911,449 A | 6/1999 | Daniele et al. |
| 5,941,706 A | 8/1999 | Ura |
| 5,951,475 A | 9/1999 | Gueziec et al. |
| 5,987,960 A | 11/1999 | Messner et al. |
| 6,012,216 A | 1/2000 | Esteves et al. |
| 6,031,888 A | 2/2000 | Ivan et al. |
| 6,033,415 A | 3/2000 | Mittelstadt et al. |
| 6,080,181 A | 6/2000 | Jensen et al. |
| 6,106,511 A | 8/2000 | Jensen |
| 6,122,541 A | 9/2000 | Cosman et al. |
| 6,144,875 A | 11/2000 | Schweikard et al. |
| 6,157,853 A | 12/2000 | Blume et al. |
| 6,167,145 A | 12/2000 | Foley et al. |
| 6,167,292 A | 12/2000 | Badano et al. |
| 6,201,984 B1 | 3/2001 | Funda et al. |
| 6,203,196 B1 | 3/2001 | Meyer et al. |
| 6,205,411 B1 | 3/2001 | DiGioia, III et al. |
| 6,212,419 B1 | 4/2001 | Blume et al. |
| 6,231,565 B1 | 5/2001 | Tovey et al. |
| 6,236,875 B1 | 5/2001 | Bucholz et al. |
| 6,246,900 B1 | 6/2001 | Cosman et al. |
| 6,301,495 B1 | 10/2001 | Gueziec et al. |
| 6,306,126 B1 | 10/2001 | Montezuma |
| 6,312,435 B1 | 11/2001 | Wallace et al. |
| 6,314,311 B1 | 11/2001 | Williams et al. |
| 6,320,929 B1 | 11/2001 | Von Der Haar |
| 6,322,567 B1 | 11/2001 | Mittelstadt et al. |
| 6,325,808 B1 | 12/2001 | Bernard et al. |
| 6,340,363 B1 | 1/2002 | Bolger et al. |
| 6,377,011 B1 | 4/2002 | Ben-Ur |
| 6,379,302 B1 | 4/2002 | Kessman et al. |
| 6,402,762 B2 | 6/2002 | Hunter et al. |
| 6,424,885 B1 | 7/2002 | Niemeyer et al. |
| 6,447,503 B1 | 9/2002 | Wynne et al. |
| 6,451,027 B1 | 9/2002 | Cooper et al. |
| 6,477,400 B1 | 11/2002 | Barrick |
| 6,484,049 B1 | 11/2002 | Seeley et al. |
| 6,487,267 B1 | 11/2002 | Wolter |
| 6,490,467 B1 | 12/2002 | Bucholz et al. |
| 6,490,475 B1 | 12/2002 | Seeley et al. |
| 6,499,488 B1 | 12/2002 | Hunter et al. |
| 6,501,981 B1 | 12/2002 | Schweikard et al. |
| 6,507,751 B2 | 1/2003 | Blume et al. |
| 6,535,756 B1 | 3/2003 | Simon et al. |
| 6,560,354 B1 | 5/2003 | Maurer, Jr. et al. |
| 6,565,554 B1 | 5/2003 | Niemeyer |
| 6,587,750 B2 | 7/2003 | Gerbi et al. |
| 6,614,453 B1 | 9/2003 | Suri et al. |
| 6,614,871 B1 | 9/2003 | Kobiki et al. |
| 6,619,840 B2 | 9/2003 | Rasche et al. |
| 6,636,757 B1 | 10/2003 | Jascob et al. |
| 6,645,196 B1 | 11/2003 | Nixon et al. |
| 6,666,579 B2 | 12/2003 | Jensen |
| 6,669,635 B2 | 12/2003 | Kessman et al. |
| 6,701,173 B2 | 3/2004 | Nowinski et al. |
| 6,757,068 B2 | 6/2004 | Foxlin |
| 6,782,287 B2 | 8/2004 | Grzeszczuk et al. |
| 6,783,524 B2 | 8/2004 | Anderson et al. |
| 6,786,896 B1 | 9/2004 | Madhani et al. |
| 6,788,018 B1 | 9/2004 | Blumenkranz |
| 6,804,581 B2 | 10/2004 | Wang et al. |
| 6,823,207 B1 | 11/2004 | Jensen et al. |
| 6,827,351 B2 | 12/2004 | Graziani et al. |
| 6,837,892 B2 | 1/2005 | Shoham |
| 6,839,612 B2 | 1/2005 | Sanchez et al. |
| 6,856,826 B2 | 2/2005 | Seeley et al. |
| 6,856,827 B2 | 2/2005 | Seeley et al. |
| 6,879,880 B2 | 4/2005 | Nowlin et al. |
| 6,892,090 B2 | 5/2005 | Verard et al. |
| 6,920,347 B2 | 7/2005 | Simon et al. |
| 6,922,632 B2 | 7/2005 | Foxlin |
| 6,968,224 B2 | 11/2005 | Kessman et al. |
| 6,978,166 B2 | 12/2005 | Foley et al. |
| 6,988,009 B2 | 1/2006 | Grimm et al. |
| 6,991,627 B2 | 1/2006 | Madhani et al. |
| 6,996,487 B2 | 2/2006 | Jutras et al. |
| 6,999,852 B2 | 2/2006 | Green |
| 7,007,699 B2 | 3/2006 | Martinelli et al. |
| 7,016,457 B1 | 3/2006 | Senzig et al. |
| 7,043,961 B2 | 5/2006 | Pandey et al. |
| 7,062,006 B1 | 6/2006 | Pelc et al. |
| 7,063,705 B2 | 6/2006 | Young et al. |
| 7,072,707 B2 | 7/2006 | Galloway, Jr. et al. |
| 7,083,615 B2 | 8/2006 | Peterson et al. |
| 7,097,640 B2 | 8/2006 | Wang et al. |
| 7,099,428 B2 | 8/2006 | Clinthorne et al. |
| 7,108,421 B2 | 9/2006 | Gregerson et al. |
| 7,130,676 B2 | 10/2006 | Barrick |
| 7,139,418 B2 | 11/2006 | Abovitz et al. |
| 7,139,601 B2 | 11/2006 | Bucholz et al. |
| 7,155,316 B2 | 12/2006 | Sutherland et al. |
| 7,164,968 B2 | 1/2007 | Treat et al. |
| 7,167,738 B2 | 1/2007 | Schweikard et al. |
| 7,169,141 B2 | 1/2007 | Brock et al. |
| 7,172,627 B2 | 2/2007 | Fiere et al. |
| 7,194,120 B2 | 3/2007 | Wicker et al. |
| 7,197,107 B2 | 3/2007 | Arai et al. |
| 7,231,014 B2 | 6/2007 | Levy |
| 7,231,063 B2 | 6/2007 | Naimark et al. |
| 7,239,940 B2 | 7/2007 | Wang et al. |
| 7,248,914 B2 | 7/2007 | Hastings et al. |
| 7,301,648 B2 | 11/2007 | Foxlin |
| 7,302,288 B1 | 11/2007 | Schellenberg |
| 7,313,430 B2 | 12/2007 | Urquhart et al. |
| 7,318,805 B2 | 1/2008 | Schweikard et al. |
| 7,318,827 B2 | 1/2008 | Leitner et al. |
| 7,319,897 B2 | 1/2008 | Leitner et al. |
| 7,324,623 B2 | 1/2008 | Heuscher et al. |
| 7,327,865 B2 | 2/2008 | Fu et al. |
| 7,331,967 B2 | 2/2008 | Lee et al. |
| 7,333,642 B2 | 2/2008 | Green |
| 7,339,341 B2 | 3/2008 | Oleynikov et al. |
| 7,366,562 B2 | 4/2008 | Dukesherer et al. |
| 7,379,790 B2 | 5/2008 | Toth et al. |
| 7,386,365 B2 | 6/2008 | Nixon |
| 7,422,592 B2 | 9/2008 | Morley et al. |
| 7,435,216 B2 | 10/2008 | Kwon et al. |
| 7,440,793 B2 | 10/2008 | Chauhan et al. |
| 7,460,637 B2 | 12/2008 | Clinthorne et al. |
| 7,466,303 B2 | 12/2008 | Yi et al. |
| 7,493,153 B2 | 2/2009 | Ahmed et al. |
| 7,505,617 B2 | 3/2009 | Fu et al. |
| 7,533,892 B2 | 5/2009 | Schena et al. |
| 7,542,791 B2 | 6/2009 | Mire et al. |
| 7,555,331 B2 | 6/2009 | Viswanathan |
| 7,567,834 B2 | 7/2009 | Clayton et al. |
| 7,594,912 B2 | 9/2009 | Cooper et al. |
| 7,606,613 B2 | 10/2009 | Simon et al. |
| 7,607,440 B2 | 10/2009 | Coste-Maniere et al. |
| 7,623,902 B2 | 11/2009 | Pacheco |
| 7,630,752 B2 | 12/2009 | Viswanathan |
| 7,630,753 B2 | 12/2009 | Simon et al. |
| 7,643,862 B2 | 1/2010 | Schoenefeld |
| 7,660,623 B2 | 2/2010 | Hunter et al. |
| 7,661,881 B2 | 2/2010 | Gregerson et al. |
| 7,683,331 B2 | 3/2010 | Chang |
| 7,683,332 B2 | 3/2010 | Chang |
| 7,689,320 B2 | 3/2010 | Prisco et al. |
| 7,691,098 B2 | 4/2010 | Wallace et al. |
| 7,702,379 B2 | 4/2010 | Avinash et al. |
| 7,702,477 B2 | 4/2010 | Tuemmler et al. |
| 7,711,083 B2 | 5/2010 | Heigl et al. |
| 7,711,406 B2 | 5/2010 | Kuhn et al. |
| 7,720,523 B2 | 5/2010 | Omernick et al. |
| 7,725,253 B2 | 5/2010 | Foxlin |
| 7,726,171 B2 | 6/2010 | Langlotz et al. |

(56) References Cited

U.S. PATENT DOCUMENTS

| | | |
|---|---|---|
| 7,742,801 B2 | 6/2010 | Neubauer et al. |
| 7,751,865 B2 | 7/2010 | Jascob et al. |
| 7,760,849 B2 | 7/2010 | Zhang |
| 7,762,825 B2 | 7/2010 | Burbank et al. |
| 7,763,015 B2 | 7/2010 | Cooper et al. |
| 7,787,699 B2 | 8/2010 | Mahesh et al. |
| 7,796,728 B2 | 9/2010 | Bergfjord |
| 7,813,838 B2 | 10/2010 | Sommer |
| 7,818,044 B2 | 10/2010 | Dukesherer et al. |
| 7,819,859 B2 | 10/2010 | Prisco et al. |
| 7,824,401 B2 | 11/2010 | Manzo et al. |
| 7,831,294 B2 | 11/2010 | Viswanathan |
| 7,834,484 B2 | 11/2010 | Sartor |
| 7,835,557 B2 | 11/2010 | Kendrick et al. |
| 7,835,778 B2 | 11/2010 | Foley et al. |
| 7,835,784 B2 | 11/2010 | Mire et al. |
| 7,840,253 B2 | 11/2010 | Tremblay et al. |
| 7,840,256 B2 | 11/2010 | Lakin et al. |
| 7,843,158 B2 | 11/2010 | Prisco |
| 7,844,320 B2 | 11/2010 | Shahidi |
| 7,853,305 B2 | 12/2010 | Simon et al. |
| 7,853,313 B2 | 12/2010 | Thompson |
| 7,865,269 B2 | 1/2011 | Prisco et al. |
| D631,966 S | 2/2011 | Perloff et al. |
| 7,879,045 B2 | 2/2011 | Gielen et al. |
| 7,881,767 B2 | 2/2011 | Strommer et al. |
| 7,881,770 B2 | 2/2011 | Melkent et al. |
| 7,886,743 B2 | 2/2011 | Cooper et al. |
| RE42,194 E | 3/2011 | Foley et al. |
| RE42,226 E | 3/2011 | Foley et al. |
| 7,900,524 B2 | 3/2011 | Calloway et al. |
| 7,907,166 B2 | 3/2011 | Lamprecht et al. |
| 7,909,122 B2 | 3/2011 | Schena et al. |
| 7,925,653 B2 | 4/2011 | Saptharishi |
| 7,930,065 B2 | 4/2011 | Larkin et al. |
| 7,935,130 B2 | 5/2011 | Williams |
| 7,940,999 B2 | 5/2011 | Liao et al. |
| 7,945,012 B2 | 5/2011 | Ye et al. |
| 7,945,021 B2 | 5/2011 | Shapiro et al. |
| 7,953,470 B2 | 5/2011 | Vetter et al. |
| 7,954,397 B2 | 6/2011 | Choi et al. |
| 7,971,341 B2 | 7/2011 | Dukesherer et al. |
| 7,974,674 B2 | 7/2011 | Hauck et al. |
| 7,974,677 B2 | 7/2011 | Mire et al. |
| 7,974,681 B2 | 7/2011 | Wallace et al. |
| 7,979,157 B2 | 7/2011 | Anvari |
| 7,983,733 B2 | 7/2011 | Viswanathan |
| 7,988,215 B2 | 8/2011 | Seibold |
| 7,996,110 B2 | 8/2011 | Lipow et al. |
| 8,004,121 B2 | 8/2011 | Sartor |
| 8,004,229 B2 | 8/2011 | Nowlin et al. |
| 8,010,177 B2 | 8/2011 | Csavoy et al. |
| 8,019,045 B2 | 9/2011 | Kato |
| 8,021,310 B2 | 9/2011 | Sanborn et al. |
| 8,035,685 B2 | 10/2011 | Jensen |
| 8,046,054 B2 | 10/2011 | Kim et al. |
| 8,046,057 B2 | 10/2011 | Clarke |
| 8,052,688 B2 | 11/2011 | Wolf, II |
| 8,054,184 B2 | 11/2011 | Cline et al. |
| 8,054,752 B2 | 11/2011 | Druke et al. |
| 8,057,397 B2 | 11/2011 | Li et al. |
| 8,057,407 B2 | 11/2011 | Martinelli et al. |
| 8,062,288 B2 | 11/2011 | Cooper et al. |
| 8,062,375 B2 | 11/2011 | Glerum et al. |
| 8,066,524 B2 | 11/2011 | Burbank et al. |
| 8,073,335 B2 | 12/2011 | Labonville et al. |
| 8,073,528 B2 * | 12/2011 | Zhao .................. G06K 9/3241 600/424 |
| 8,079,950 B2 | 12/2011 | Stern et al. |
| 8,086,299 B2 | 12/2011 | Adler et al. |
| 8,092,370 B2 | 1/2012 | Roberts et al. |
| 8,098,914 B2 | 1/2012 | Liao et al. |
| 8,100,950 B2 | 1/2012 | St. Clair et al. |
| 8,105,320 B2 | 1/2012 | Manzo |
| 8,108,025 B2 | 1/2012 | Csavoy et al. |
| 8,109,877 B2 | 2/2012 | Moctezuma de la Barrera et al. |
| 8,112,292 B2 | 2/2012 | Simon |
| 8,116,430 B1 | 2/2012 | Shapiro et al. |
| 8,120,301 B2 | 2/2012 | Goldberg et al. |
| 8,121,249 B2 | 2/2012 | Wang et al. |
| 8,123,675 B2 | 2/2012 | Funda et al. |
| 8,133,229 B1 | 3/2012 | Bonutti |
| 8,142,420 B2 | 3/2012 | Schena |
| 8,147,494 B2 | 4/2012 | Leitner et al. |
| 8,150,494 B2 | 4/2012 | Simon et al. |
| 8,150,497 B2 | 4/2012 | Gielen et al. |
| 8,150,498 B2 | 4/2012 | Gielen et al. |
| 8,165,658 B2 | 4/2012 | Waynik et al. |
| 8,170,313 B2 | 5/2012 | Kendrick et al. |
| 8,179,073 B2 | 5/2012 | Farritor et al. |
| 8,182,476 B2 | 5/2012 | Julian et al. |
| 8,184,880 B2 | 5/2012 | Zhao et al. |
| 8,202,278 B2 | 6/2012 | Orban, III et al. |
| 8,208,708 B2 | 6/2012 | Homan et al. |
| 8,208,988 B2 | 6/2012 | Jensen |
| 8,219,177 B2 | 7/2012 | Smith et al. |
| 8,219,178 B2 | 7/2012 | Smith et al. |
| 8,220,468 B2 | 7/2012 | Cooper et al. |
| 8,224,024 B2 | 7/2012 | Foxlin et al. |
| 8,224,484 B2 | 7/2012 | Swarup et al. |
| 8,225,798 B2 | 7/2012 | Baldwin et al. |
| 8,228,368 B2 | 7/2012 | Zhao et al. |
| 8,231,610 B2 | 7/2012 | Jo et al. |
| 8,263,933 B2 | 7/2012 | Hartmann et al. |
| 8,239,001 B2 | 8/2012 | Verard et al. |
| 8,241,271 B2 | 8/2012 | Millman et al. |
| 8,248,413 B2 | 8/2012 | Gattani et al. |
| 8,256,319 B2 | 9/2012 | Cooper et al. |
| 8,271,069 B2 | 9/2012 | Jascob et al. |
| 8,271,130 B2 | 9/2012 | Hourtash |
| 8,281,670 B2 | 10/2012 | Larkin et al. |
| 8,282,653 B2 | 10/2012 | Nelson et al. |
| 8,301,226 B2 | 10/2012 | Csavoy et al. |
| 8,311,611 B2 | 11/2012 | Csavoy et al. |
| 8,320,991 B2 | 11/2012 | Jascob et al. |
| 8,332,012 B2 | 12/2012 | Kienzle, III |
| 8,333,755 B2 | 12/2012 | Cooper et al. |
| 8,335,552 B2 | 12/2012 | Stiles |
| 8,335,557 B2 | 12/2012 | Maschke |
| 8,348,931 B2 | 1/2013 | Cooper et al. |
| 8,353,963 B2 | 1/2013 | Glerum |
| 8,358,818 B2 | 1/2013 | Miga et al. |
| 8,359,730 B2 | 1/2013 | Burg et al. |
| 8,374,673 B2 | 2/2013 | Adcox et al. |
| 8,374,723 B2 | 2/2013 | Zhao et al. |
| 8,379,791 B2 | 2/2013 | Forthmann et al. |
| 8,386,019 B2 | 2/2013 | Camus et al. |
| 8,392,022 B2 | 3/2013 | Ortmaier et al. |
| 8,394,099 B2 | 3/2013 | Patwardhan |
| 8,395,342 B2 | 3/2013 | Prisco |
| 8,398,634 B2 | 3/2013 | Manzo et al. |
| 8,400,094 B2 | 3/2013 | Schena |
| 8,414,957 B2 | 4/2013 | Enzerink et al. |
| 8,418,073 B2 | 4/2013 | Mohr et al. |
| 8,450,694 B2 | 5/2013 | Baviera et al. |
| 8,452,447 B2 | 5/2013 | Nixon |
| RE44,305 E | 6/2013 | Foley et al. |
| 8,462,911 B2 | 6/2013 | Vesel et al. |
| 8,465,476 B2 | 6/2013 | Rogers et al. |
| 8,465,771 B2 | 6/2013 | Wan et al. |
| 8,467,851 B2 | 6/2013 | Mire et al. |
| 8,467,852 B2 | 6/2013 | Csavoy et al. |
| 8,469,947 B2 | 6/2013 | Devengenzo et al. |
| RE44,392 E | 7/2013 | Hynes |
| 8,483,434 B2 | 7/2013 | Buehner et al. |
| 8,483,800 B2 | 7/2013 | Jensen et al. |
| 8,486,532 B2 | 7/2013 | Enzerink et al. |
| 8,489,235 B2 | 7/2013 | Moll et al. |
| 8,500,722 B2 | 8/2013 | Cooper |
| 8,500,728 B2 | 8/2013 | Newton et al. |
| 8,504,201 B2 | 8/2013 | Moll et al. |
| 8,506,555 B2 | 8/2013 | Ruiz Morales |
| 8,506,556 B2 | 8/2013 | Schena |
| 8,508,173 B2 | 8/2013 | Goldberg et al. |

(56) References Cited

U.S. PATENT DOCUMENTS

| | | |
|---|---|---|
| 8,512,318 B2 | 8/2013 | Tovey et al. |
| 8,515,576 B2 | 8/2013 | Lipow et al. |
| 8,518,120 B2 | 8/2013 | Glerum et al. |
| 8,521,331 B2 | 8/2013 | Itkowitz |
| 8,526,688 B2 | 9/2013 | Groszmann et al. |
| 8,526,700 B2 | 9/2013 | Isaacs |
| 8,527,094 B2 | 9/2013 | Kumar et al. |
| 8,528,440 B2 | 9/2013 | Morley et al. |
| 8,532,741 B2 | 9/2013 | Heruth et al. |
| 8,541,970 B2 | 9/2013 | Nowlin et al. |
| 8,548,563 B2 | 10/2013 | Simon et al. |
| 8,549,732 B2 | 10/2013 | Burg et al. |
| 8,551,114 B2 | 10/2013 | Ramos de la Pena |
| 8,551,116 B2 | 10/2013 | Julian et al. |
| 8,556,807 B2 | 10/2013 | Scott et al. |
| 8,556,979 B2 | 10/2013 | Glerum et al. |
| 8,560,118 B2 | 10/2013 | Green et al. |
| 8,561,473 B2 | 10/2013 | Blumenkranz |
| 8,562,594 B2 | 10/2013 | Cooper et al. |
| 8,571,638 B2 | 10/2013 | Shoham |
| 8,571,710 B2 | 10/2013 | Coste-Maniere et al. |
| 8,573,465 B2 | 11/2013 | Shelton, IV |
| 8,574,303 B2 | 11/2013 | Sharkey et al. |
| 8,585,420 B2 | 11/2013 | Burbank et al. |
| 8,594,841 B2 | 11/2013 | Zhao et al. |
| 8,597,198 B2 | 12/2013 | Sanborn et al. |
| 8,600,478 B2 | 12/2013 | Verard et al. |
| 8,603,077 B2 | 12/2013 | Cooper et al. |
| 8,611,985 B2 | 12/2013 | Lavallee et al. |
| 8,613,230 B2 | 12/2013 | Blumenkranz et al. |
| 8,621,939 B2 | 1/2014 | Blumenkranz et al. |
| 8,624,537 B2 | 1/2014 | Nowlin et al. |
| 8,630,389 B2 | 1/2014 | Kato |
| 8,634,897 B2 | 1/2014 | Simon et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,639,000 B2 | 1/2014 | Zhao et al. |
| 8,641,726 B2 | 2/2014 | Bonutti |
| 8,644,907 B2 | 2/2014 | Hartmann et al. |
| 8,657,809 B2 | 2/2014 | Schoepp |
| 8,660,635 B2 | 2/2014 | Simon et al. |
| 8,666,544 B2 | 3/2014 | Moll et al. |
| 8,675,939 B2 | 3/2014 | Moctezuma de la Barrera |
| 8,678,647 B2 | 3/2014 | Gregerson et al. |
| 8,679,125 B2 | 3/2014 | Smith et al. |
| 8,679,183 B2 | 3/2014 | Glerum et al. |
| 8,682,413 B2 | 3/2014 | Lloyd |
| 8,684,253 B2 | 4/2014 | Giordano et al. |
| 8,685,098 B2 | 4/2014 | Glerum et al. |
| 8,693,730 B2 | 4/2014 | Umasuthan et al. |
| 8,694,075 B2 | 4/2014 | Groszmann et al. |
| 8,696,458 B2 | 4/2014 | Foxlin et al. |
| 8,700,123 B2 | 4/2014 | Okamura et al. |
| 8,706,086 B2 | 4/2014 | Glerum |
| 8,706,185 B2 | 4/2014 | Foley et al. |
| 8,706,301 B2 | 4/2014 | Zhao et al. |
| 8,709,045 B1 | 4/2014 | Folsom |
| 8,717,430 B2 | 5/2014 | Simon et al. |
| 8,727,618 B2 | 5/2014 | Maschke et al. |
| 8,734,432 B2 | 5/2014 | Tuma et al. |
| 8,738,115 B2 | 5/2014 | Amberg et al. |
| 8,738,181 B2 | 5/2014 | Greer et al. |
| 8,740,882 B2 | 6/2014 | Jun et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,761,930 B2 | 6/2014 | Nixon |
| 8,764,448 B2 | 7/2014 | Yang et al. |
| 8,771,170 B2 | 7/2014 | Mesallum et al. |
| 8,781,186 B2 | 7/2014 | Clements et al. |
| 8,781,630 B2 | 7/2014 | Banks et al. |
| 8,784,385 B2 | 7/2014 | Boyden et al. |
| 8,786,241 B2 | 7/2014 | Nowlin et al. |
| 8,787,520 B2 | 7/2014 | Baba |
| 8,792,704 B2 | 7/2014 | Isaacs |
| 8,798,231 B2 | 8/2014 | Notohara et al. |
| 8,800,838 B2 | 8/2014 | Shelton, IV |
| 8,808,164 B2 | 8/2014 | Hoffman et al. |
| 8,812,077 B2 | 8/2014 | Dempsey |
| 8,814,793 B2 | 8/2014 | Brabrand |
| 8,816,628 B2 | 8/2014 | Nowlin et al. |
| 8,818,105 B2 | 8/2014 | Myronenko et al. |
| 8,820,605 B2 | 9/2014 | Shelton, IV |
| 8,821,511 B2 | 9/2014 | Von Jako et al. |
| 8,823,308 B2 | 9/2014 | Nowlin et al. |
| 8,827,996 B2 | 9/2014 | Scott et al. |
| 8,828,024 B2 | 9/2014 | Farritor et al. |
| 8,830,224 B2 | 9/2014 | Zhao et al. |
| 8,834,489 B2 | 9/2014 | Cooper et al. |
| 8,834,490 B2 | 9/2014 | Bonutti |
| 8,838,270 B2 | 9/2014 | Druke et al. |
| 8,844,789 B2 | 9/2014 | Shelton, IV et al. |
| 8,855,822 B2 | 10/2014 | Bartol et al. |
| 8,858,598 B2 | 10/2014 | Seifert et al. |
| 8,860,753 B2 | 10/2014 | Bhandarkar et al. |
| 8,864,751 B2 | 10/2014 | Prisco et al. |
| 8,864,798 B2 | 10/2014 | Weiman et al. |
| 8,864,833 B2 | 10/2014 | Glerum et al. |
| 8,867,703 B2 | 10/2014 | Shapiro et al. |
| 8,870,880 B2 | 10/2014 | Himmelberger et al. |
| 8,876,866 B2 | 11/2014 | Zappacosta et al. |
| 8,880,223 B2 | 11/2014 | Raj et al. |
| 8,882,803 B2 | 11/2014 | Iott et al. |
| 8,883,210 B1 | 11/2014 | Truncale et al. |
| 8,888,821 B2 | 11/2014 | Rezach et al. |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,688 B2 | 11/2014 | Suh |
| 8,894,691 B2 | 11/2014 | Iott et al. |
| 8,906,069 B2 | 12/2014 | Hansell et al. |
| 8,964,934 B2 | 2/2015 | Ein-Gal |
| 8,992,580 B2 | 3/2015 | Bar et al. |
| 8,996,169 B2 | 3/2015 | Lightcap et al. |
| 9,001,963 B2 | 4/2015 | Sowards-Emmerd et al. |
| 9,002,076 B2 | 4/2015 | Khadem et al. |
| 9,044,190 B2 | 6/2015 | Rubner et al. |
| 9,107,683 B2 | 8/2015 | Hourtash et al. |
| 9,125,556 B2 | 9/2015 | Zehavi et al. |
| 9,131,986 B2 | 9/2015 | Greer et al. |
| 9,215,968 B2 | 12/2015 | Schostek et al. |
| 9,241,771 B2 * | 1/2016 | Kostrzewski ...... A61B 17/1703 |
| 9,308,050 B2 | 4/2016 | Kostrzewski et al. |
| 9,380,984 B2 | 7/2016 | Li |
| 9,393,039 B2 | 7/2016 | Lechner et al. |
| 9,398,886 B2 | 7/2016 | Gregerson et al. |
| 9,398,890 B2 | 7/2016 | Dong et al. |
| 9,414,859 B2 | 8/2016 | Ballard et al. |
| 9,420,975 B2 | 8/2016 | Gutfleisch et al. |
| 9,492,235 B2 | 11/2016 | Hourtash et al. |
| 9,592,096 B2 | 3/2017 | Maillet et al. |
| 9,750,465 B2 | 9/2017 | Engel et al. |
| 9,750,510 B2 * | 9/2017 | Kostrzewski .......... A61B 17/17 |
| 9,757,203 B2 | 9/2017 | Hourtash et al. |
| 9,795,354 B2 | 10/2017 | Menegaz et al. |
| 9,814,535 B2 | 11/2017 | Bar et al. |
| 9,820,783 B2 | 11/2017 | Donner et al. |
| 9,833,265 B2 | 11/2017 | Donner et al. |
| 9,848,922 B2 | 12/2017 | Tohmeh et al. |
| 9,925,011 B2 | 3/2018 | Gombert et al. |
| 9,931,025 B1 | 4/2018 | Graetzel et al. |
| 10,034,717 B2 | 7/2018 | Miller et al. |
| 10,357,257 B2 * | 7/2019 | Kostrzewski .......... A61B 34/20 |
| 10,548,620 B2 * | 2/2020 | Kostrzewski ...... A61B 17/1703 |
| 2001/0036302 A1 | 11/2001 | Miller |
| 2002/0035321 A1 | 3/2002 | Bucholz et al. |
| 2004/0068172 A1 | 4/2004 | Nowinski et al. |
| 2004/0076259 A1 | 4/2004 | Jensen et al. |
| 2004/0265082 A1 | 12/2004 | Abrams |
| 2005/0096502 A1 | 5/2005 | Khalili |
| 2005/0143651 A1 | 6/2005 | Verard et al. |
| 2005/0171558 A1 | 8/2005 | Abovitz et al. |
| 2006/0100610 A1 | 5/2006 | Wallace et al. |

(56) References Cited

U.S. PATENT DOCUMENTS

| | | |
|---|---|---|
| 2006/0173329 A1 | 8/2006 | Marquart et al. |
| 2006/0184396 A1 | 8/2006 | Dennis et al. |
| 2006/0241416 A1 | 10/2006 | Marquart et al. |
| 2006/0291612 A1 | 12/2006 | Nishide et al. |
| 2007/0015987 A1 | 1/2007 | Benlloch Baviera et al. |
| 2007/0021738 A1 | 1/2007 | Hasser et al. |
| 2007/0038059 A1 | 2/2007 | Sheffer et al. |
| 2007/0073133 A1 | 3/2007 | Schoenefeld |
| 2007/0156121 A1 | 7/2007 | Millman et al. |
| 2007/0156157 A1 | 7/2007 | Nahum et al. |
| 2007/0167712 A1 | 7/2007 | Keglovich et al. |
| 2007/0233238 A1 | 10/2007 | Huynh et al. |
| 2007/0239187 A1 | 10/2007 | Brunnett |
| 2007/0293867 A1 | 12/2007 | Anitua |
| 2008/0004523 A1 | 1/2008 | Jensen |
| 2008/0013809 A1 | 1/2008 | Zhu et al. |
| 2008/0033283 A1 | 2/2008 | Dellaca et al. |
| 2008/0046122 A1 | 2/2008 | Manzo et al. |
| 2008/0082109 A1 | 4/2008 | Moll et al. |
| 2008/0108912 A1 | 5/2008 | Node-Langlois |
| 2008/0108991 A1 | 5/2008 | Von Jako |
| 2008/0109012 A1 | 5/2008 | Falco et al. |
| 2008/0144906 A1 | 6/2008 | Allred et al. |
| 2008/0161680 A1 | 7/2008 | Von Jako et al. |
| 2008/0161682 A1 | 7/2008 | Kendrick et al. |
| 2008/0177203 A1 | 7/2008 | von Jako |
| 2008/0214922 A1 | 9/2008 | Hartmann et al. |
| 2008/0228068 A1 | 9/2008 | Viswanathan et al. |
| 2008/0228196 A1 | 9/2008 | Wang et al. |
| 2008/0235052 A1 | 9/2008 | Node-Langlois et al. |
| 2008/0269596 A1 | 10/2008 | Revie et al. |
| 2008/0287771 A1 | 11/2008 | Anderson |
| 2008/0287781 A1 | 11/2008 | Revie et al. |
| 2008/0300477 A1 | 12/2008 | Lloyd et al. |
| 2008/0300478 A1 | 12/2008 | Zuhars et al. |
| 2008/0302950 A1 | 12/2008 | Park et al. |
| 2008/0306490 A1 | 12/2008 | Lakin et al. |
| 2008/0319311 A1 | 12/2008 | Hamadeh |
| 2009/0012509 A1 | 1/2009 | Csavoy et al. |
| 2009/0024129 A1 | 1/2009 | Gordon et al. |
| 2009/0030428 A1 | 1/2009 | Omori et al. |
| 2009/0080737 A1 | 3/2009 | Battle et al. |
| 2009/0185655 A1 | 7/2009 | Koken et al. |
| 2009/0198121 A1 | 8/2009 | Hoheisel |
| 2009/0216113 A1 | 8/2009 | Meier et al. |
| 2009/0228019 A1 | 9/2009 | Gross et al. |
| 2009/0259123 A1 | 10/2009 | Navab et al. |
| 2009/0259230 A1 | 10/2009 | Khadem et al. |
| 2009/0264899 A1 | 10/2009 | Appenrodt et al. |
| 2009/0281417 A1 | 11/2009 | Hartmann et al. |
| 2009/0287222 A1 | 11/2009 | Lee et al. |
| 2010/0022874 A1 | 1/2010 | Wang et al. |
| 2010/0039506 A1 | 2/2010 | Sarvestani et al. |
| 2010/0125286 A1 | 5/2010 | Wang et al. |
| 2010/0130986 A1 | 5/2010 | Mailloux et al. |
| 2010/0145341 A1 | 6/2010 | Ranck et al. |
| 2010/0228117 A1 | 9/2010 | Hartmann |
| 2010/0228265 A1 | 9/2010 | Pnsco |
| 2010/0249571 A1 | 9/2010 | Jensen et al. |
| 2010/0274120 A1 | 10/2010 | Heuscher |
| 2010/0280363 A1 | 11/2010 | Skarda et al. |
| 2010/0331858 A1 | 12/2010 | Simaan et al. |
| 2011/0022229 A1 | 1/2011 | Jang et al. |
| 2011/0077504 A1 | 3/2011 | Fischer et al. |
| 2011/0098553 A1 | 4/2011 | Robbins et al. |
| 2011/0137152 A1 | 6/2011 | Li |
| 2011/0213384 A1 | 9/2011 | Jeong |
| 2011/0224684 A1 | 9/2011 | Larkin et al. |
| 2011/0224685 A1 | 9/2011 | Larkin et al. |
| 2011/0224686 A1 | 9/2011 | Larkin et al. |
| 2011/0224687 A1 | 9/2011 | Larkin et al. |
| 2011/0224688 A1 | 9/2011 | Larkin et al. |
| 2011/0224689 A1 | 9/2011 | Larkin et al. |
| 2011/0224825 A1 | 9/2011 | Larkin et al. |
| 2011/0230967 A1 | 9/2011 | O'Halloran et al. |
| 2011/0238080 A1 | 9/2011 | Ranjit et al. |
| 2011/0276058 A1 | 11/2011 | Choi et al. |
| 2011/0282189 A1 | 11/2011 | Graumann |
| 2011/0286573 A1 | 11/2011 | Schretter et al. |
| 2011/0295062 A1 | 12/2011 | Gratacos Solsona et al. |
| 2011/0295370 A1 | 12/2011 | Suh et al. |
| 2011/0306986 A1 | 12/2011 | Lee et al. |
| 2012/0035507 A1 | 2/2012 | George et al. |
| 2012/0046668 A1 | 2/2012 | Gantes |
| 2012/0051498 A1 | 3/2012 | Koishi |
| 2012/0053597 A1 | 3/2012 | Anvari et al. |
| 2012/0059248 A1 | 3/2012 | Holsing et al. |
| 2012/0071753 A1 | 3/2012 | Hunter et al. |
| 2012/0108954 A1 | 5/2012 | Schulhauser et al. |
| 2012/0136372 A1 | 5/2012 | Amat Girbau et al. |
| 2012/0143084 A1 | 6/2012 | Shoham |
| 2012/0184839 A1 | 7/2012 | Woerlein |
| 2012/0197182 A1 | 8/2012 | Millman et al. |
| 2012/0226145 A1 | 9/2012 | Chang et al. |
| 2012/0235909 A1 | 9/2012 | Birkenbach et al. |
| 2012/0245596 A1 | 9/2012 | Meenink |
| 2012/0253332 A1 | 10/2012 | Moll |
| 2012/0253360 A1 | 10/2012 | White et al. |
| 2012/0256092 A1 | 10/2012 | Zingerman |
| 2012/0294498 A1 | 11/2012 | Popovic |
| 2012/0296203 A1 | 11/2012 | Hartmann et al. |
| 2012/0330315 A1 | 12/2012 | Ranck et al. |
| 2013/0006267 A1 | 1/2013 | Odermatt et al. |
| 2013/0016889 A1 | 1/2013 | Myronenko et al. |
| 2013/0030571 A1 | 1/2013 | Ruiz Morales et al. |
| 2013/0035583 A1 | 2/2013 | Park et al. |
| 2013/0060146 A1 | 3/2013 | Yang et al. |
| 2013/0060337 A1 | 3/2013 | Petersheim et al. |
| 2013/0094742 A1 | 4/2013 | Feilkas |
| 2013/0096574 A1 | 4/2013 | Kang et al. |
| 2013/0113791 A1 | 5/2013 | Isaacs et al. |
| 2013/0116706 A1 | 5/2013 | Lee et al. |
| 2013/0131695 A1 | 5/2013 | Scarfogliero et al. |
| 2013/0144307 A1 | 6/2013 | Jeong et al. |
| 2013/0158542 A1 | 6/2013 | Manzo et al. |
| 2013/0165937 A1 | 6/2013 | Patwardhan |
| 2013/0178867 A1 | 7/2013 | Farritor et al. |
| 2013/0178868 A1 | 7/2013 | Roh |
| 2013/0178870 A1 | 7/2013 | Schena |
| 2013/0204271 A1 | 8/2013 | Brisson et al. |
| 2013/0211419 A1 | 8/2013 | Jensen |
| 2013/0211420 A1 | 8/2013 | Jensen |
| 2013/0218142 A1 | 8/2013 | Tuma et al. |
| 2013/0223702 A1 | 8/2013 | Holsing et al. |
| 2013/0225942 A1 | 8/2013 | Holsing et al. |
| 2013/0225943 A1 | 8/2013 | Holsing et al. |
| 2013/0231556 A1 | 9/2013 | Holsing et al. |
| 2013/0237995 A1 | 9/2013 | Lee et al. |
| 2013/0245375 A1 | 9/2013 | DiMaio et al. |
| 2013/0261640 A1 | 10/2013 | Kim et al. |
| 2013/0272488 A1 | 10/2013 | Bailey et al. |
| 2013/0272489 A1 | 10/2013 | Dickman et al. |
| 2013/0274761 A1 | 10/2013 | Devengenzo et al. |
| 2013/0281821 A1 | 10/2013 | Liu et al. |
| 2013/0296884 A1 | 11/2013 | Taylor et al. |
| 2013/0303887 A1 | 11/2013 | Holsing et al. |
| 2013/0307955 A1 | 11/2013 | Deitz et al. |
| 2013/0317521 A1 | 11/2013 | Choi et al. |
| 2013/0325033 A1 | 12/2013 | Schena et al. |
| 2013/0325035 A1 | 12/2013 | Hauck et al. |
| 2013/0331686 A1 | 12/2013 | Freysinger et al. |
| 2013/0331858 A1 | 12/2013 | Devengenzo et al. |
| 2013/0331861 A1 | 12/2013 | Yoon |
| 2013/0342578 A1 | 12/2013 | Isaacs |
| 2013/0345717 A1 | 12/2013 | Markvicka et al. |
| 2013/0345757 A1 | 12/2013 | Stad |
| 2014/0001235 A1 | 1/2014 | Shelton, IV |
| 2014/0012131 A1 | 1/2014 | Heruth et al. |
| 2014/0031664 A1 | 1/2014 | Kang et al. |
| 2014/0046128 A1 | 2/2014 | Lee et al. |
| 2014/0046132 A1 | 2/2014 | Hoeg et al. |
| 2014/0046340 A1 | 2/2014 | Wilson et al. |
| 2014/0049629 A1 | 2/2014 | Siewerdsen et al. |
| 2014/0058406 A1 | 2/2014 | Tsekos |

(56) References Cited

U.S. PATENT DOCUMENTS

| | | |
|---|---|---|
| 2014/0073914 A1 | 3/2014 | Lavallee et al. |
| 2014/0080086 A1 | 3/2014 | Chen |
| 2014/0081128 A1 | 3/2014 | Verard et al. |
| 2014/0088612 A1 | 3/2014 | Bartol et al. |
| 2014/0094694 A1 | 4/2014 | Moctezuma de la Barrera |
| 2014/0094851 A1 | 4/2014 | Gordon |
| 2014/0096369 A1 | 4/2014 | Matsumoto et al. |
| 2014/0100587 A1 | 4/2014 | Farritor et al. |
| 2014/0121676 A1 | 5/2014 | Kostrzewski et al. |
| 2014/0128882 A1 | 5/2014 | Kwak et al. |
| 2014/0135796 A1 | 5/2014 | Simon et al. |
| 2014/0142591 A1 | 5/2014 | Alvarez et al. |
| 2014/0142592 A1 | 5/2014 | Moon et al. |
| 2014/0148692 A1 | 5/2014 | Hartmann et al. |
| 2014/0163581 A1 | 6/2014 | Devengenzo et al. |
| 2014/0171781 A1 | 6/2014 | Stiles |
| 2014/0171900 A1 | 6/2014 | Stiles |
| 2014/0171965 A1 | 6/2014 | Loh et al. |
| 2014/0180308 A1 | 6/2014 | von Grunberg |
| 2014/0180309 A1 | 6/2014 | Seeber et al. |
| 2014/0187915 A1 | 7/2014 | Yaroshenko et al. |
| 2014/0188132 A1 | 7/2014 | Kang |
| 2014/0194699 A1 | 7/2014 | Roh et al. |
| 2014/0130810 A1 | 8/2014 | Azizian et al. |
| 2014/0221819 A1 | 8/2014 | Sarment |
| 2014/0222023 A1 | 8/2014 | Kim et al. |
| 2014/0228631 A1 | 8/2014 | Kwak et al. |
| 2014/0234804 A1 | 8/2014 | Huang et al. |
| 2014/0257328 A1 | 9/2014 | Kim et al. |
| 2014/0257329 A1 | 9/2014 | Jang et al. |
| 2014/0257330 A1 | 9/2014 | Choi et al. |
| 2014/0275760 A1 | 9/2014 | Lee et al. |
| 2014/0275985 A1 | 9/2014 | Walker et al. |
| 2014/0276931 A1 | 9/2014 | Parihar et al. |
| 2014/0276940 A1 | 9/2014 | Seo |
| 2014/0276944 A1 | 9/2014 | Farritor et al. |
| 2014/0288413 A1 | 9/2014 | Hwang et al. |
| 2014/0299648 A1 | 10/2014 | Shelton, IV et al. |
| 2014/0303434 A1 | 10/2014 | Farritor et al. |
| 2014/0303643 A1 | 10/2014 | Ha et al. |
| 2014/0305995 A1 | 10/2014 | Shelton, IV et al. |
| 2014/0309659 A1 | 10/2014 | Roh et al. |
| 2014/0316436 A1 | 10/2014 | Bar et al. |
| 2014/0323803 A1 | 10/2014 | Hoffman et al. |
| 2014/0324070 A1 | 10/2014 | Min et al. |
| 2014/0330288 A1 | 11/2014 | Date et al. |
| 2014/0364720 A1 | 12/2014 | Darrow et al. |
| 2014/0371577 A1 | 12/2014 | Mallet et al. |
| 2015/0039034 A1 | 2/2015 | Frankel et al. |
| 2015/0085970 A1 | 3/2015 | Bouhnik et al. |
| 2015/0146847 A1 | 5/2015 | Liu |
| 2015/0150524 A1 | 6/2015 | Yorkston et al. |
| 2015/0196261 A1 | 7/2015 | Funk |
| 2015/0196365 A1* | 7/2015 | Kostrzewski .......... A61B 17/17 606/130 |
| 2015/0213633 A1 | 7/2015 | Chang et al. |
| 2015/0335480 A1 | 11/2015 | Alvarez et al. |
| 2015/0342647 A1 | 12/2015 | Frankel et al. |
| 2016/0005194 A1 | 1/2016 | Schretter et al. |
| 2016/0008011 A1 | 1/2016 | Kostrzewski |
| 2016/0106442 A1 | 4/2016 | Guo et al. |
| 2016/0151120 A1 | 6/2016 | Kostrzewski et al. |
| 2016/0166329 A1 | 6/2016 | Langan et al. |
| 2016/0235480 A1 | 8/2016 | Scholl et al. |
| 2016/0249990 A1 | 9/2016 | Glozman et al. |
| 2016/0302871 A1 | 10/2016 | Gregerson et al. |
| 2016/0320322 A1 | 11/2016 | Suzuki |
| 2016/0331335 A1 | 11/2016 | Gregerson et al. |
| 2017/0135770 A1 | 5/2017 | Scholl et al. |
| 2017/0143284 A1 | 5/2017 | Sehnert et al. |
| 2017/0143426 A1 | 5/2017 | Isaacs et al. |
| 2017/0156816 A1 | 6/2017 | Ibrahim |
| 2017/0202629 A1 | 7/2017 | Maillet et al. |
| 2017/0212723 A1 | 7/2017 | Atarot et al. |
| 2017/0215825 A1 | 8/2017 | Johnson et al. |
| 2017/0215826 A1 | 8/2017 | Johnson et al. |
| 2017/0215827 A1 | 8/2017 | Johnson et al. |
| 2017/0231710 A1 | 8/2017 | Scholl et al. |
| 2017/0258426 A1 | 9/2017 | Risher-Kelly et al. |
| 2017/0273748 A1 | 9/2017 | Hourtash et al. |
| 2017/0296277 A1 | 10/2017 | Hourtash et al. |
| 2017/0360493 A1 | 12/2017 | Zucher et al. |

FOREIGN PATENT DOCUMENTS

| | | |
|---|---|---|
| EP | 2698115 A1 | 2/2014 |
| WO | 2011147831 A1 | 12/2011 |

* cited by examiner

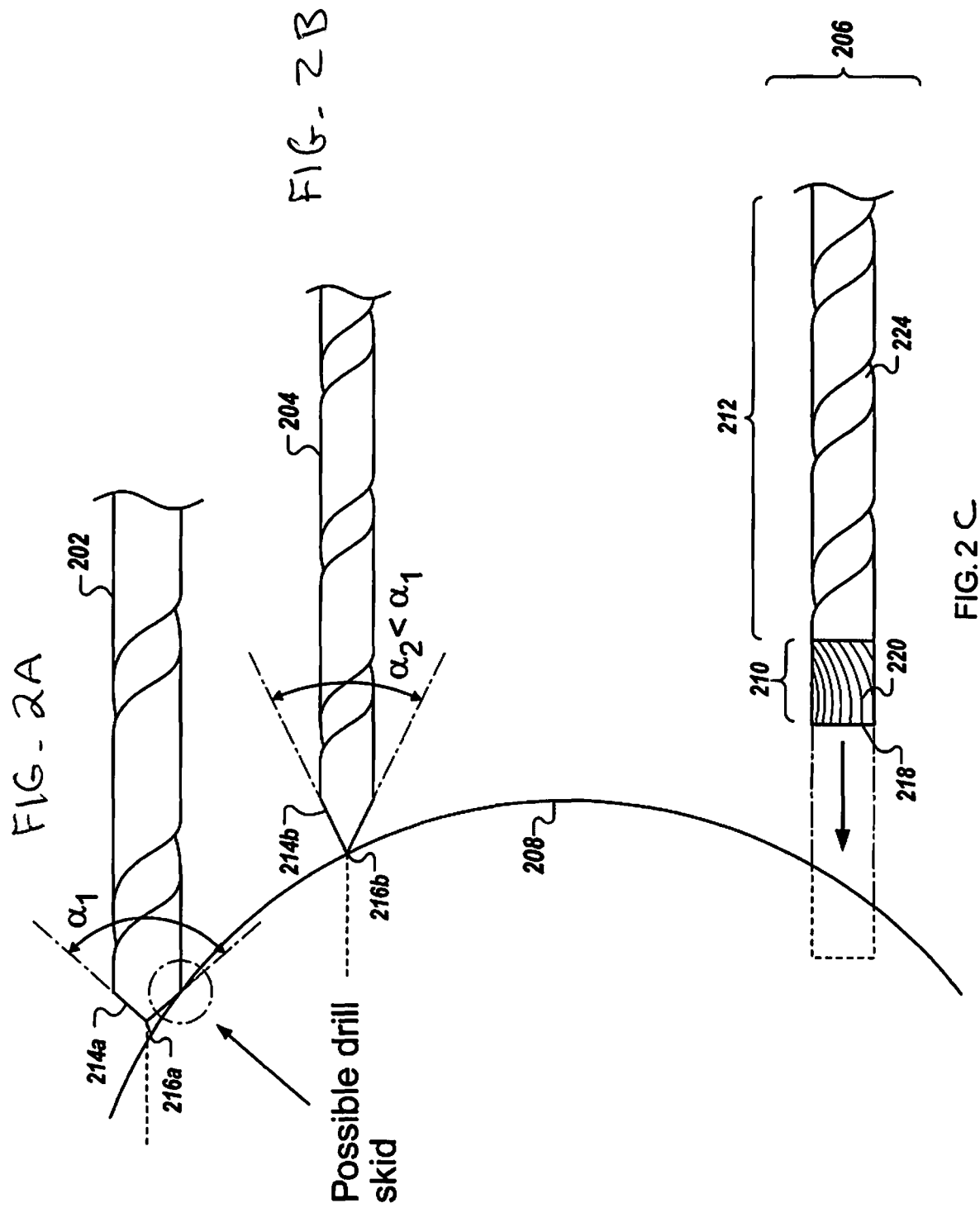

ANTI-SKID SURGICAL INSTRUMENT FOR USE IN PREPARING HOLES IN BONE TISSUE

PRIORITY APPLICATION

This application is a continuation application of U.S. patent application Ser. No. 14/799,170 filed on Jul. 14, 2015 which claims priority to and the benefit of U.S. Provisional Patent Application No. 62/024,402, filed Jul. 14, 2014, entitled "Anti-Skid Surgical Instrument for use in Preparing Holes in Bone Tissue," the contents of which is incorporated by reference herein in its entirety.

FIELD OF THE INVENTION

The present invention relates to an anti-skid surgical instrument for use in preparing holes in bone tissue during an operation.

BACKGROUND OF THE INVENTION

Spinal surgeries often require precision drilling and placement of screws or other implements in bone tissue. Catastrophic damage or death may result from improper drilling or maneuvering of the body during spinal surgery due to the proximity of the spinal cord and arteries. Further, accurate placement is typically necessary for a successful outcome. For example, spinal fusion is typically augmented by stabilizing the vertebrae with fixation devices, such as metallic screws, rods, and plates, to facilitate bone fusion. In spinal fusion, as well as other surgeries, the accuracy with which the screws are placed in the bone has a direct effect on the outcome of the procedure. The less motion there is between the two bones trying to heal, the higher the change the bones will successfully fuse. The use of fixation devices has increased the success rate of spinal fusion procedures considerably.

Such procedures rely strongly on the expertise of the surgeon, and there is significant variation in success rate among different surgeons. A number of navigational and verification approaches have been developed. However, screw misplacement is still a common problem in such surgical procedures. Screws may be misaligned due to inaccurate holes drilled prior to inserting the screw. The angle of the tip of the drill may cause the drill bit to skid as the tip contacts the bone tissue, thereby causing the hole to be drilled along an incorrect trajectory. Typically, unless a bone drill is driven at 90 degrees to the bone surface there is a tendency for the drill bit to skid over the bone surface thereby placing the hole inappropriately. Thus, there is a need for an anti-skid surgical instrument for preparing holes in a patient's bone while minimizing the risk of the instrument skidding upon contact of the surgical instrument with the bone.

SUMMARY OF THE INVENTION

Described herein is an anti-skid surgical instrument for use in preparing holes in bone tissue. The disclosed surgical instrument provides the ability to prepare a precise hole in bone tissue during surgery (e.g., spinal surgeries and pedicle screw placement, intramedullary screw placement). The disclosed surgical instrument accomplishes precise hole placement regardless of whether the angle between the drill axis and surface of the bone tissue is perpendicular. The disclosed technology includes a flat drilling surface which is perpendicular to the surface of the body of the surgical instrument. This reduces the likelihood of the surgical instrument skidding on the surface of the bone tissue and thereby increases the precision of the hole.

In one aspect, the disclosed technology includes an anti-skid surgical instrument for preparing a hole in bone tissue of a patient during surgery. In certain embodiments, the anti-skid surgical instrument has an elongate structure including: a mill head at the end of the elongate structure for removing bone tissue with reduced skidding (e.g., unintentional lateral movement of the surgical instrument) of the surgical instrument upon contact of the anti-ski surgical instrument with the bone tissue, wherein the mill head has a flat end substantially perpendicular to a longitudinal axis of the elongate structure, and one or more side-cutting flutes about the longitudinal axis of the elongate structure for cutting into bone tissue; a shank for connection to a drill, and a shaft between the mill head and the shank, the shaft having one or more drill flutes (e.g., non-cutting flutes) for evacuating removed bone tissue.

In certain embodiments, the flat end of the mill head has one or more end cutting flutes for cutting axially into the bone tissue.

In certain embodiments, the one or more drill flutes are different than the one or more side cutting flutes.

In certain embodiments, the one or more drill flutes include two, three, four, six, eight, ten, or twenty flutes.

In certain embodiments, one or more side cutting flutes include two, three, four, six, eight, ten, or twenty flutes.

In certain embodiments, a longitudinal length of the shaft is greater than a longitudinal length of the mill head.

In certain embodiments, a longitudinal length of the shaft is greater than a longitudinal length of the shank.

In certain embodiments, the one or more drill flutes have a higher twist rate (i.e., larger flute angle) than the one or more side cutting flutes.

In certain embodiments, the one or more drill flutes have a lower twist rate (i.e., smaller flute angle) than the one or more side cutting flutes.

In certain embodiments, the one or more drill flutes have a different twist rate (i.e., different flute angle) than the one or more side cutting flutes.

In certain embodiments, the surgery is spinal, orthopedic, dental, ear, nose, or throat surgery.

In certain embodiments, the anti-skid surgical instrument is insertable into a surgical instrument guide such that the surgical instrument is constrained by the surgical instrument guide.

In certain embodiments, the surgical instrument guide includes a rigid hollow tubular structure having a first open end and a second open end, said structure defining an axis of the tubular structure along which movement of a surgical instrument sliding through the structure is restricted, wherein the tubular structure has an interior surface shaped and sized to accommodate the anti-skid surgical instrument sliding through the guide such that movement of the anti-skid surgical instrument (e.g., fitted with a tool support) is constrained in all directions except along the axis defined by the guide.

In certain embodiments, the anti-skid surgical instrument is fitted with a tool support shaped and sized to slide through the surgical instrument guide along the axis defined by the guide.

In certain embodiments, the anti-skid surgical instrument is a drill bit and the surgical instrument guide is a drill bit guide.

In certain embodiments, the anti-skid surgical instrument is configured to be guided by a robotic surgical system including a robotic arm.

In certain embodiments, the robotic arm has an end effector including a surgical instrument guide attached thereto, the surgical instrument guide configured to hold and/or restrict movement of a surgical instrument therethrough.

In certain embodiments, a navigation marker is used by a navigation camera to track the anti-skid surgical instrument.

In certain embodiments, the surgical instrument guide is configured to be used to guide a screw implant and a tissue protector.

In certain embodiments, a manipulator is attached to the robotic arm.

In certain embodiments, the manipulator is molded into the robotic arm.

In certain embodiments, the axis of the surgical instrument guide can be aligned with the desired trajectory in relation to the patient situation via the manipulator.

In another aspect, the disclosed technology includes a method of performing surgery using an anti-skid surgical instrument to prepare a hole in bone tissue of a patient. In certain embodiments, the method includes maneuvering the anti-skid surgical instrument to prepare the hole in the bone tissue of the patient, wherein the anti-skid surgical instrument having an elongate structure including: a mill head at the end of the elongate structure for removing bone tissue with reduced skidding (e.g., unintentional lateral movement of the surgical instrument) of the surgical instrument upon contact of the anti-ski surgical instrument with the bone tissue, wherein the mill head has a flat end substantially perpendicular to a longitudinal axis of the elongate structure, and one or more side-cutting flutes about the longitudinal axis of the elongate structure for cutting into bone tissue; a shank for connection to a drill, and a shaft between the mill head and the shank, the shaft having one or more drill flutes (e.g., non-cutting flutes) for evacuating removed bone tissue.

In certain embodiments, maneuvering the anti-skid surgical instrument includes inserting the surgical instrument into a surgical instrument guide such that the surgical instrument is constrained by the surgical instrument guide.

In certain embodiments, the surgical instrument guide includes a rigid hollow tubular structure having a first open end and a second open end, said structure defining an axis of the tubular structure along which movement of a surgical instrument sliding through the structure is restricted, wherein the tubular structure has an interior surface shaped and sized to accommodate the anti-skid surgical instrument sliding through the guide such that movement of the anti-skid surgical instrument (e.g., fitted with a tool support) is constrained in all directions except along the axis defined by the guide.

In certain embodiments, the anti-skid surgical instrument is fitted with a tool support shaped and sized to slide through the surgical instrument guide along the axis defined by the guide.

In certain embodiments, the anti-skid surgical instrument is a drill bit and the surgical instrument guide is a drill bit guide.

In certain embodiments, the anti-ski surgical instrument is for use in at least one of spinal, orthopedic, dental, ear, nose, and throat surgery.

In certain embodiments, the anti-skid surgical instrument is guided by a robotic surgical system including a robotic arm.

In certain embodiments, the robotic arm has an end effector including a surgical instrument guide attached thereto, the surgical instrument guide configured to hold and/or restrict movement of a surgical instrument therethrough.

In certain embodiments, the method includes fixing the position of the robotic arm (and, therefore, the position of the surgical instrument guide).

In certain embodiments, a navigation marker is used by a navigation camera to track the anti-skid surgical instrument.

In certain embodiments, the method includes obtaining or accessing a CT scan, 3D CT scan, fluoroscopy, 3D fluoroscopy, or natural landmark-based image of the patient situation.

In certain embodiments, a manipulator is attached to the robotic arm.

In certain embodiments, the manipulator is molded into the robotic arm.

In certain embodiments, the axis can be aligned with the desired trajectory in relation to the patient situation via the manipulator.

In certain embodiments, the flat end of the mill head has one or more end cutting flutes for cutting axially into the bone tissue.

In certain embodiments, the one or more drill flutes are different than the one or more side cutting flutes.

In certain embodiments, the one or more drill flutes include two, three, four, six, eight, ten, or twenty flutes.

In certain embodiments, one or more side cutting flutes include two, three, four, six, eight, ten, or twenty flutes.

In certain embodiments, a longitudinal length of the shaft is greater than a longitudinal length of the mill head.

In certain embodiments, a longitudinal length of the shaft is greater than a longitudinal length of the shank.

In certain embodiments, the one or more drill flutes have a higher twist rate (i.e., larger flute angle) than the one or more side cutting flutes.

In certain embodiments, the one or more drill flutes have a lower twist rate (i.e., smaller flute angle) than the one or more side cutting flutes.

In certain embodiments, the one or more drill flutes have a different twist rate (i.e., different flute angle) than the one or more side cutting flutes.

BRIEF DESCRIPTION OF THE FIGURES

The foregoing and other objects, aspects, features, and advantages of the present disclosure will become more apparent and better understood by referring to the following description taken in conjunction with the accompanying drawings, in which:

FIG. 2A is an example surgical instrument used for preparing holes in bone tissue;

FIG. 2B is another example of a surgical instrument used for preparing holes in bone tissue; and FIG. 2C is yet another example of a surgical instrument used for preparing holes in bone tissue.

Figure 1:
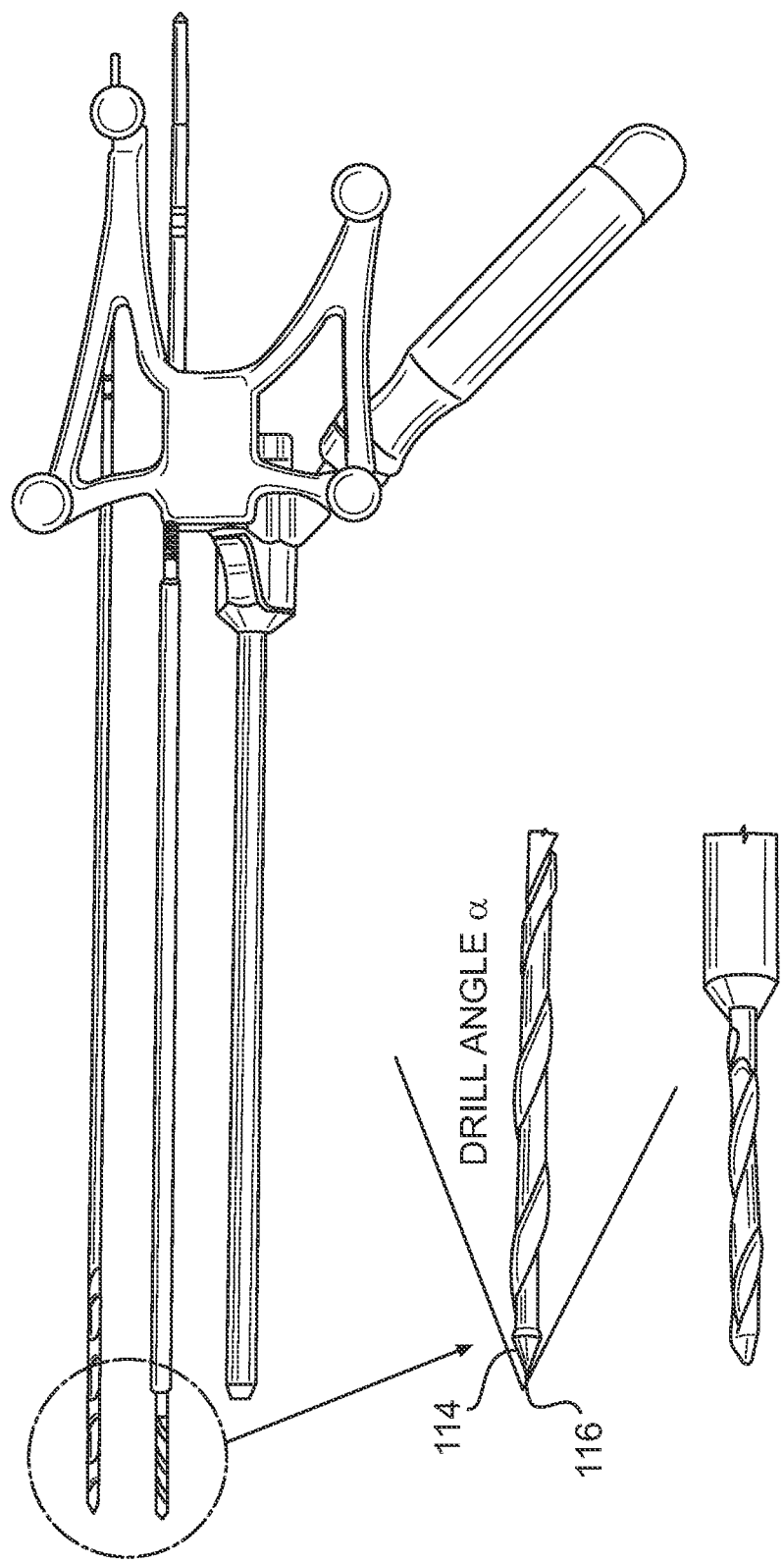
FIG. 1 is an illustration of example drill bits for preparing holes in bone tissue.

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION

Described herein is an anti-skid surgical instrument for use in preparing holes in bone tissue. In certain types of surgeries, it is necessary to prepare a precise hole in bone tissue (e.g. spinal surgeries and pedicle screw placement, intramedullary screw placement); however, in many instances, human anatomy is not well adapted for drilling in these regions because the angle between the drill axis and surface of the bone is not perpendicular. The disclosed technology provides the ability to precisely prepare a hole in bone tissue by minimizing the likelihood that the surgical instrument skids upon contact with bone tissue.

As used herein, the phrase "prepare a hole in bone tissue" encompasses milling, drilling, grinding, and/or cutting bone tissue and/or bone-like tissue. A "hole" encompasses any cavity, dent, or depression.

FIG. 1 is an illustration of example prior art drill bits 102 and 104 and an example surgical instrument guide 106. Typically, surgical instruments include a tapered end 114 that narrows to a point 116. The point 116 is used to guide the drill bit. Standard surgical instruments, especially drill bits, may skid on the surface of bone tissue which significantly decreases precision of the hole. The skidding can be linked with drill angle α which is not well adapted to drilling at an angle (different from the right angle) to the bone tissue surface. Given that the surface of most bones are not perfectly flat, standard drill bits often result in imprecise holes in the bone. For example, if the side of the drill (e.g., the side of the tapered tip 114 of the drill) touches the bone tissue before tip 116 of the drill bit has entered the tissue and provides guidance, drill skid is more likely.

FIGS. 2A-C illustrate a comparison of three drill bits contacting the surface of bone tissue 208. As shown in FIG. 2A, drill bit 202 is likely to skid because the tip 216a of the drill bit 202 will not contract the surface of the bone tissue 208 first. Instead, the side 214a of the tapered tip will contract the bone tissue 208 before the tip 216a. In contrast, the tip 216b of drill bit 204 is less likely to skid because the tip 216b of the drill bit 204 contracts the bone tissue 208 first as shown in FIG. 2B. However, one of the reasons it is difficult to predict if and when a drill bit will skid during surgeries is the difficulty of determining whether the tip of the drill bit will contract the bone tissue 208 first.

The anti-skid surgical instrument 206 as shown in FIG. 2C reduces the risk of drill bit skid because the "tip" is a flat milling surface 218 which is perpendicular to the surface of the body of the surgical instrument. The mill head 210 of the anti-skid surgical instrument 206 is adapted for milling (e.g., rather than drilling) when entering the bone tissue 208. The portion of the instrument body 212 after the head 210, in some implementations, is adapted for drilling (e.g., contains evacuating holes, spirals, twists, etc.).

In some implementations, the anti-skid surgical instrument 206 has a mill head 210 at the end of the elongate structure for removing bone tissue with reduced skidding (e.g., unintentional lateral movement of the surgical instrument) of the surgical instrument upon contact of the anti-ski surgical instrument with the bone tissue 208. The mill head 210 has a flat end 218 substantially perpendicular to a longitudinal axis of the elongate structure. In some implementations, the mill head 210 has one or more side-cutting flutes 220 (e.g., sharpened) about the longitudinal axis of the elongate structure for cutting into bone tissue. The one or more side cutting flutes 220 can include two, three, four, six, eight, ten, or twenty flutes.

In some implementations, the anti-skid surgical instrument 206 has a shank (not shown) for connection to a drill. In some implementations, the anti-skid surgical instrument 206 has a shaft 212 between the mill head 210 and the shank, the shaft 212 having one or more drill flutes 224 (e.g., non-cutting flutes; e.g., unsharpened) for evacuating removed bone tissue. In some implementations, the one or more drill flutes 224 include two, three, four, six, eight, ten, or twenty flutes. The one or more drill flutes 224 are different than the one or more side cutting flutes 220. For example, the drill flutes 224 may have a different (e.g., larger or smaller) twist rate, (e.g., flute angle) than the side cutting flutes 220.

In some implementations, the flat end 218 of the mill head 210 has one or more end cutting flutes (not shown) for cutting axially into the bone tissue. In some implementations, the one or more end cutting flutes are cutting teeth. Additionally, a longitudinal length of the shaft, in some implementations, is greater than a longitudinal length of the mill head. The longitudinal length of the shaft, in some implementations, is less than a longitudinal length of the mill head.

As shown in FIG. 2C, the anti-skid surgical instrument 206 has an elongate structure with a mill head 210 with milling surface 218, a shaft 212 with a drill surface. In some implementations, the instrument 206 includes a second end, opposite the first end 210, with a shank configured to be grasped by a drill. The mill head 210 of the anti-skid surgical instrument 206 is flat and substantially perpendicular to the surface of the elongate structure, thereby reducing skidding (e.g., unintentional lateral movement of the surgical instrument 206) of the surgical instrument 206 upon contact of the milling surface 218 with bone tissue 208.

The mill end 210, in some implementations, utilizes rotary cutters to remove material. The mill end 210 can take the form of several shapes and sizes. For example, the mill end 210 can be an end mill, slab mill, or other types of milling devices.

The flutes 220 of the mill head 210, in some implementations, are deep helical grooves running up the cutter, while the sharp blade along the edge of the flute 220 is known as the tooth. The tooth cuts the material, and chips of this material are pulled up the flute 220 by the rotation of the cutter. In some implementations, there is one tooth per flute. In some implementations, there are two or more teeth per flute. For example, the cutter of each flute 220 may have 2, 3, 4, 5, or more teeth (e.g., 1-4, 5-10, or 10-20 teeth). Typically, the more teeth a cutter has, the more rapidly it can remove material. Thus, typically a 4-tooth cutter can remove material at twice the rate of a 2-tooth cutter. The mill head 210 may be an end mill with cutting teeth at one end (i.e., the flat end 218) and on the sides 220 of mill end 210. For example, the flat end 218 can be a flat bottom cutter.

In some implementations, the surgical instrument 206 is rigidly guided (e.g., by a robotic surgical system). The surgical instrument 206 may cause higher radial forces when entering bone tissue 208, thus a rigid guide ensures that the hole will be placed accurately. The drill used with the surgical instrument 206, in some implementations, is sufficiently rigid to avoid deflection of the drill itself. A high rotational velocity drill (e.g., power drill) may be used to reduce radial forces.

In some implementations, the surgical instrument 206 is used in combination with a robotic surgical system. In some implementations, the surgical instrument 206 is used with a passive arm or any device that provides rigid fixation of the surgical instrument 206. The surgical instrument 206 may be insertable into a surgical instrument guide such that the surgical instrument 206 is constrained by the surgical instrument guide. The surgical instrument guide may include a rigid hollow tubular structure having a first open end and a second open end. The structure of the guide may define the axis along which movement of a surgical instrument sliding through the structure is restricted. The tubular structure may have an interior surface shaped and sized to accommodate the anti-skid surgical instrument 206 sliding through the guide such that movement of the surgical instrument 206 (e.g., fitted with a tool support) is constrained in all directions except along the axis defined by the guide. The surgical instrument 206 may be fitted with or have an integrated tool support such that the tool support engages the guide to provide accurate guidance of the surgical instrument 206. For example, the anti-skid surgical instrument 206 may be fitted with a tool support shaped and sized to slide through the surgical instrument guide along the axis defined by the guide.

In instances in which the surgical instrument 206 is guided by a robotic surgical system, the robotic surgical system may include a robotic arm. In some implementations, the robotic arm has an end effector including a surgical instrument guide attached thereto, the surgical instrument guide configured to hold and/or restrict movement of a surgical instrument therethrough. A navigation marker may be used to track the surgical instrument 206. The axis of the surgical instrument guide can be aligned with the desired trajectory in relation to the patient situation via the manipulator.

In view of the structure, functions and apparatus of the systems and methods described here, in some implementations, a system and method for performing surgery with a robotic surgical system are provided. Having described certain implementations of methods and apparatus for supporting a robotic surgical system, it will now become apparent to one of skill in the art that other implementations incorporating the concepts of the disclosure may be used. Therefore, the disclosure should not be limited to certain implementations, but rather should be limited only by the spirit and scope of the following claims.

Throughout the description, where apparatus and systems are described as having, including, or comprising specific components, or where processes and methods are described as having, including, or comprising specific steps, it is contemplated that, additionally, there are apparatus, and systems of the disclosed technology that consist essentially of, or consist of, the recited components, and that there are processes and methods according to the disclosed technology that consist essentially of, or consist of, the recited processing steps.

It should be understood that the order of steps or order for performing certain action is immaterial so long as the disclosed technology remains operable. Moreover, two or more steps or actions may be conducted simultaneously.

What is claimed:

1. A method of performing surgery using an anti-skid surgical instrument to prepare a hole in bone tissue of a patient, the method comprising:
    maneuvering the anti-skid surgical instrument to prepare the hole in the bone tissue of the patient, wherein the anti-skid surgical instrument includes:
        a mill head for removing bone tissue with reduced skidding of the surgical instrument upon contact of the anti-skid surgical instrument with the bone tissue, wherein the mill head has a flat end substantially perpendicular to a longitudinal axis, and one or more side-cutting flutes about the longitudinal axis for cutting into bone tissue;
        a shank for connection to a drill, and
        a shaft between the mill head and the shank, the shaft having one or more drill flutes for evacuating removed bone tissue,
        wherein the mill head and the shaft together define a cylindrical elongate structure and the maximum diameter of the mill head and the shaft is substantially the same, and wherein the anti-skid surgical instrument is guided by a robotic surgical system comprising a robotic arm.

2. The method of claim 1, wherein maneuvering the anti-skid surgical instrument comprises inserting the surgical instrument into a surgical instrument guide such that the surgical instrument is constrained by the surgical instrument guide.

3. The method of claim 2, wherein the surgical instrument guide comprises a rigid hollow tubular structure having a first open end and a second open end, said structure defining an axis of the tubular structure along which movement of a surgical instrument sliding through the structure is restricted, wherein the tubular structure has an interior surface shaped and sized to accommodate the anti-skid surgical instrument sliding through the guide such that movement of the anti-skid surgical instrument is constrained in all directions except along the axis defined by the guide.

4. The method of claim 3, wherein the anti-skid surgical instrument is fitted with a tool support shaped and sized to slide through the surgical instrument guide along the axis defined by the guide.

5. The method of claim 2, wherein the anti-skid surgical instrument is a drill bit and the surgical instrument guide is a drill bit guide.

6. The method of claim 1, wherein the flat end of the mill head includes end-cutting flutes.

7. The method of claim 1, wherein the robotic arm has an end effector comprising a surgical instrument guide attached thereto, the surgical instrument guide configured to hold and/or restrict movement of a surgical instrument therethrough.

8. The method of claim 1, further comprising: fixing the position of the robotic arm wherein the flat end includes a milling surface.

9. The method of claim 1, wherein a navigation marker is used by a navigation camera to track the anti-skid surgical instrument.

10. The method of claim 1, comprising: obtaining or accessing a CT scan, 3D CT scan, fluoroscopy, 3D fluoroscopy, or natural landmark-based image of the patient situation.

11. The method of claim 1, wherein a manipulator is attached to the robotic arm.

12. The method of claim 1, wherein the manipulator is molded into the robotic arm.

13. The method of claim 1, wherein the axis can be aligned with the desired trajectory in relation to the patient situation via the manipulator.

14. A method of performing surgery using an anti-skid surgical instrument to prepare a hole in bone tissue of a patient, the method comprising:
    maneuvering the anti-skid surgical instrument to prepare the hole in the bone tissue of the patient, wherein the anti-skid surgical instrument includes:
        a mill head for removing bone tissue with reduced skidding of the surgical instrument upon contact of the anti-skid surgical instrument with the bone tissue, wherein the mill head has a flat end substantially perpendicular to a longitudinal axis, and one or more side-cutting flutes about the longitudinal axis for cutting into bone tissue;

a shank for connection to a drill, and a shaft between the mill head and the shank, the shaft having one or more drill flutes for evacuating removed bone tissue, wherein the mill head and the shaft together define a cylindrical elongate structure, the flat head of the mill head includes a milling surface, wherein a maximum diameter of the mill head is substantially the same as the maximum diameter of the shaft, and wherein the anti-skid surgical instrument is guided by a robotic surgical system comprising a robotic arm.

15. The method of claim 14, wherein maneuvering the anti-skid surgical instrument comprises inserting the surgical instrument into a surgical instrument guide such that the surgical instrument is constrained by the surgical instrument guide.

16. The method of claim 15, wherein the surgical instrument guide comprises a rigid hollow tubular structure having a first open end and a second open end, said structure defining an axis of the tubular structure along which movement of a surgical instrument sliding through the structure is restricted, wherein the tubular structure has an interior surface shaped and sized to accommodate the anti-skid surgical instrument sliding through the guide such that movement of the anti-skid surgical instrument is constrained in all directions except along the axis defined by the guide.

17. The method of claim 16, wherein the anti-skid surgical instrument is fitted with a tool support shaped and sized to slide through the surgical instrument guide along the axis defined by the guide.

18. The method of claim 15, wherein the anti-skid surgical instrument is a drill bit and the surgical instrument guide is a drill bit guide.

19. The method of claim 14, wherein the robotic arm has an end effector comprising a surgical instrument guide attached thereto, the surgical instrument guide configured to hold and/or restrict movement of a surgical instrument therethrough.

* * * * *